US011426081B2

(12) United States Patent
Lee et al.

(10) Patent No.: US 11,426,081 B2
(45) Date of Patent: Aug. 30, 2022

(54) VASCULAR BRANCH CHARACTERIZATION (71) Applicant: PACESETTER, INC., Sylmar, CA (US)

(72) Inventors: Kwangdeok Lee, Santa Clarita, CA (US); Edward Karst, Los Angeles, CA (US); Michael E. Benser, Valencia, CA (US); Rohan More, Los Angeles, CA (US); Craig Hewitt, San Diego, CA (US); Stuart Rosenberg, Castaic, CA (US); Fujian Qu, San Jose, CA (US); Hoda Razavi, San Jose, CA (US)

(73) Assignee: PACESETTER, INC., Sylmar, CA (US)

( * ) Notice: Subject to any disclaimer, the term of this patent is extended or adjusted under 35 U.S.C. 154(b) by 571 days.

(21) Appl. No.: 15/017,283

(22) Filed: Feb. 5, 2016

(65) Prior Publication Data

US 2016/0150980 A1 Jun. 2, 2016

Related U.S. Application Data (62) Division of application No. 13/783,014, filed on Mar. 1, 2013, now Pat. No. 9,282,916.

(51) Int. Cl.
*A61B 5/02* (2006.01)
*A61B 5/107* (2006.01)
(Continued)

(52) U.S. Cl.
CPC ............ *A61B 5/02007* (2013.01); *A61B 5/06* (2013.01); *A61B 5/1076* (2013.01); *A61B 5/1102* (2013.01); *A61B 5/113* (2013.01); *A61B 5/4887* (2013.01); *A61B 6/12* (2013.01); *A61B 6/503* (2013.01); *A61B 6/504* (2013.01); *A61B 6/5217* (2013.01); *A61B 8/0841* (2013.01); *A61B 8/0883* (2013.01); *A61B 8/0891* (2013.01); *A61B 8/5223* (2013.01); *A61B 5/05* (2013.01); *A61B 5/061* (2013.01); *A61B 5/065* (2013.01);
(Continued)

(58) Field of Classification Search
CPC ......... A61B 8/0841; A61B 6/12; A61B 5/062; A61B 2576/00; A61B 34/20; A61B 5/7278; A61B 8/5207
USPC .............................................. 600/424; 607/28
See application file for complete search history.

(56) References Cited

U.S. PATENT DOCUMENTS 8,285,377 B2 10/2012 Rosenberg et al.
2002/0120188 A1* 8/2002 Brock ................. A61B 5/0086
600/407
(Continued)

OTHER PUBLICATIONS

Contour, merriam-webster.com (Year: 2021).*
(Continued)

*Primary Examiner* — Alexandra L Newton
(74) *Attorney, Agent, or Firm* — The Small Patent Law Group LLC; Dean D. Small (57) ABSTRACT An apparatus and method for characterizing a region of interest (ROI) including measuring position and orientation data within the ROI; and generating a geometric data set to include one or more of: length, bifurcation location, angle and curvature characteristics of the ROI. Also, sequentially taking an image of a tool within the ROI; comparing tool dimensions with ROI dimensions; and estimating diameter, length, take-off angle, and/or tortuosity characteristics based on the comparisons.

9 Claims, 8 Drawing Sheets (51) Int. Cl.
*A61B 6/12* (2006.01)
*A61B 6/00* (2006.01)
*A61B 8/08* (2006.01)
*A61B 5/06* (2006.01)
*A61B 5/11* (2006.01)
*A61B 5/113* (2006.01)
*A61B 5/00* (2006.01)
*A61B 5/05* (2021.01)
*A61N 1/37* (2006.01)
*A61B 8/00* (2006.01)
*A61B 5/283* (2021.01)

(52) U.S. Cl.
CPC .............. *A61B 5/066* (2013.01); *A61B 5/283* (2021.01); *A61B 6/469* (2013.01); *A61B 8/469* (2013.01); *A61N 1/371* (2013.01)

(56) References Cited

U.S. PATENT DOCUMENTS

| | | | |
|---|---|---|---|
| 2003/0023198 A1 | 1/2003 | Twardowski | |
| 2004/0158211 A1 | 8/2004 | Rogers et al. | |
| 2005/0033135 A1 | 2/2005 | Govari | |
| 2005/0033164 A1 | 2/2005 | Yatsuo et al. | |
| 2005/0124864 A1* | 6/2005 | Mack | A61B 5/024 600/300 |
| 2006/0095022 A1 | 5/2006 | Moll et al. | |
| 2006/0178586 A1* | 8/2006 | Dobak, III | A61B 5/02 600/508 |
| 2007/0038062 A1 | 2/2007 | Redel | |
| 2007/0265813 A1* | 11/2007 | Unal | G06T 7/0012 703/2 |
| 2008/0021336 A1* | 1/2008 | Dobak, III | A61B 5/021 600/508 |
| 2008/0221439 A1* | 9/2008 | Iddan | A61B 6/5217 600/424 |
| 2009/0118610 A1 | 5/2009 | Karmarkar | |
| 2010/0076503 A1 | 3/2010 | Beyar et al. | |
| 2010/0082087 A1 | 4/2010 | Silipo | |
| 2010/0168561 A1* | 7/2010 | Anderson | A61B 17/32 600/424 |
| 2010/0171819 A1* | 7/2010 | Tolkowsky | G06T 7/0022 348/65 |
| 2011/0054559 A1* | 3/2011 | Rosenberg | A61N 1/3684 607/28 |
| 2011/0066201 A1 | 3/2011 | Rosenberg et al. | |
| 2012/0143278 A1 | 6/2012 | Ryu et al. | |
| 2012/0158079 A1 | 6/2012 | Rosenberg et al. | |
| 2012/0197340 A1* | 8/2012 | Tesfayesus | A61N 1/3601 607/42 |
| 2013/0066399 A1 | 3/2013 | Min | |
| 2014/0121470 A1* | 5/2014 | Scharf | A61B 5/0422 600/301 |

OTHER PUBLICATIONS

Data, The Hutchinson Unabridged Encyclopedia with Atlas and Weather Guide (Year: 2018).*
Data set, dictionary.com (Year: 2021).*
Determine, merriam-webster.com (Year: 2021).*
Dimension, The Chambers Dictionary (Year: 2015).*
Geometric, merriam-webster.com (Year: 2021).*
Geometry, merriam-webster.com (Year: 2021).*
Geometry, The Penguin Dictionary of Mathematics (Year: 2008).*
Mitral regurgitation, The American Heritage Dictionary of Medicine (Year: 2015).*
Restriction Requirement, dated Nov. 6, 2014—Parent U.S. Appl. No. 13/783,014.
NonFinal Office Action, dated Mar. 17, 2015—Parent U.S. Appl. No. 13/783,014.
Notice of Allowance, dated Jan. 5, 2016—Parent U.S. Appl. No. 13/783,014.

* cited by examiner

VASCULAR BRANCH CHARACTERIZATION

CROSS REFERENCE TO RELATED APPLICATIONS

This application is a division of U.S. patent application Ser. No. 13/783,014, filed Mar. 1, 2013.

FIELD

This disclosure relates generally to techniques for characterizing an area in a body. More particularly, the disclosure relates to characterizing vascular branches.

BACKGROUND

Cardiac resynchronization therapy is achieved by positioning a lead in a traditional location in the right ventricle (RV), and by maneuvering a left ventricular (LV) pacing lead transvenously to a target wall in the left ventricle. Delivery of an LV lead to a desired location through the coronary sinus into the veins and their side branches surrounding the left ventricle is oftentimes a challenging procedure, requiring extensive fluoroscopic exposure for the patient and clinician. Venous anatomy is also highly variable, with some patients lacking suitable veins for permanent placement of a lead at a desired site, or requiring a lead to be maneuvered through sharp or even acute takeoff angles. Navigating a challenging anatomy may increase the possibility of complications such as coronary sinus or coronary vein dissection or perforation.

Fluoroscopic imaging during transvenous LV lead implantation may involve recording one or more two-dimensional (2D) cine loops depicting objects such as the lead within the heart during implantation and at the final position. Soft tissues tend to form outlines, rather than explicitly visible objects. Although the lead may be visible, it is implanted based on comparing real-time views of the lead as it is advanced into position with a pre-recorded venogram acquired with contrast agent to highlight the coronary sinus and its venous tributaries, or by using anatomical landmarks such as the spine. However, it may still not be possible to reach a certain branch with a lead due to small vein size, acute angulation, or tortuosity of the vein. It is oftentimes challenging to know a priori whether a particular lead would fit well within a particular branch and in which branch the lead would have a low chance of dislodgement. Furthermore, there are a variety of lead models with different lengths and diameters available, but the implanting physician may not be able to determine before the actual implant procedure whether a particular lead will fit in a particular branch. Thus, it would be desirous to be able to characterize the coronary venous vasculature prior to the implantation of a permanent lead.

SUMMARY

According to one aspect, a method for characterizing a region of interest (ROI) including positioning a tool within a region of interest (ROI), wherein the tool includes a sensor; measuring one or more position data and orientation data as the sensor travels within the ROI; and generating a geometric data set of the ROI based on the measured one or more position data and orientation data, wherein the geometric data set includes one or more of the following: length, bifurcation location, angle and curvature characteristics of the ROI.

According to another aspect, a device for characterizing a region of interest (ROI) comprising a processor and a memory, the memory containing program code executable by the processor for performing the following: measuring one or more position data and orientation data as a tool with an embedded sensor travels within the ROI; and generating a geometric data set of the ROI based on the measured one or more position data and orientation data, wherein the geometric data set includes one or more of the following: length, bifurcation location, angle and curvature characteristics of the ROI.

According to another aspect, a method for characterizing a region of interest (ROI) including sequentially taking one or more visual images of a tool positioned within one or more branches of the region of interest (ROI); using the one or more visual images for comparing one or more dimensions of the tool with one or more dimensions of the one or more branches to obtain one or more comparisons; and estimating a plurality of one or more of the following: a diameter dimension, a length dimension, a take-off angle, and a tortuosity characteristic of the one or more branches based on the one or more comparisons.

According to another aspect, a device for characterizing a region of interest (ROI) comprising a processor and a memory, the memory containing program code executable by the processor for performing the following: sequentially taking one or more visual images of a tool positioned within one or more branches of the region of interest (ROI); using the one or more visual images for comparing one or more dimensions of the tool with one or more dimensions of the one or more branches to obtain one or more comparisons; and estimating a plurality of one or more of the following: a diameter dimension, a length dimension, a take-off angle, and a tortuosity characteristic of the one or more branches based on the one or more comparisons.

According to another aspect, a method for characterizing a region of interest (ROI) including collecting vibratory motion data at one or more of a plurality of locations within the region of interest (ROI) using a sensor for sensing vibratory motion; extracting one or more of a cardiac vibratory motion data or a respiratory vibratory motion data from the collected vibratory motion data to obtain residual vibratory motion data at the one or more of the plurality of locations; and generating a geometric data set of the ROI based on the residual vibratory motion data.

According to another aspect, a device for characterizing a region of interest (ROI) comprising a processor and a memory, the memory containing program code executable by the processor for performing the following: collecting vibratory motion data at one or more of a plurality of locations within the region of interest (ROI) using a sensor for sensing vibratory motion; extracting one or more of a cardiac vibratory motion data or a respiratory vibratory motion data from the collected vibratory motion data to obtain residual vibratory motion data at the one or more of the plurality of locations; and generating a geometric data set of the ROI based on the residual vibratory motion data.

According to another aspect, a method for characterizing a region of interest (ROI) including pacing a plurality of locations within the ROI with at least one pacing tool set at a first pacing level to determine a first plurality of reactions corresponding to the plurality of locations; pacing one or more of the plurality of locations with the at least one pacing tool set at a second pacing level, wherein the second pacing level is different from the first pacing level, to determine a second plurality of reactions corresponding to the plurality of locations; and generating a geometric data set of the ROI to indicate the first and second plurality of reactions, wherein the first and second plurality of reactions include one or more of the following: pacing capture threshold, presence of diaphragmatic stimulation and cardiac performance corresponding to each of the plurality of locations at each of the first and second pacing levels.

According to another aspect, a device for characterizing a region of interest (ROI) comprising a processor and a memory, the memory containing program code executable by the processor for performing the following: pacing a plurality of locations within the ROI with at least one pacing tool set at a first pacing level to determine a first plurality of reactions corresponding to the plurality of locations; pacing one or more of the plurality of locations with the at least one pacing tool set at a second pacing level, wherein the second pacing level is different from the first pacing level, to determine a second plurality of reactions corresponding to the plurality of locations; and generating a geometric data set of the ROI to indicate the first and second plurality of reactions, wherein the first and second plurality of reactions include one or more of the following: pacing capture threshold, presence of diaphragmatic stimulation and cardiac performance corresponding to each of the plurality of locations at each of the first and second pacing levels.

Advantages of the present disclosure may include allowing a priori selection of a best suitable or a preferred target site prior to lead implantation, allowing the ability to prioritize candidate target sites, and giving the implanting medical personnel increased confidence that a selected lead is likely to be safely implanted into a patient, that the lead implantation is likely to be located at an effective site, that acute and/or chronic complications are likely reduced and/or that the need for lead repositioning is likely reduced.

It is understood that other aspects will become readily apparent to those skilled in the art from the following detailed description, wherein it is shown and described in various aspects by way of illustration. The drawings and detailed description are to be regarded as illustrative in nature and not as restrictive.

DETAILED DESCRIPTION

The detailed description set forth below in connection with the appended drawings is intended as a description of various aspects of the present disclosure and is not intended to represent the only aspects in which the present disclosure may be practiced. Each aspect described in this disclosure is provided merely as an example or illustration of the present disclosure, and should not necessarily be construed as preferred or advantageous over other aspects. The detailed description includes specific details for the purpose of providing a thorough understanding of the present disclosure. However, it will be apparent to those skilled in the art that the present disclosure may be practiced without these specific details. In some instances, well-known structures and devices are shown in block diagram form in order to avoid obscuring the concepts of the present disclosure. Acronyms and other descriptive terminology may be used merely for convenience and clarity and are not intended to limit the scope of the present disclosure.

In one aspect, the present disclosure relates to characterizing a region of interest (ROI) within the body of a patient. In one example, the length of a vascular branch is measured by advancing a sensor embedded on a tool along the length of the vascular branch and measuring the distance the sensor has traveled based on its trajectory. In one example, the sensor provides real-time position and orientation information. And, the sensor is embedded on an electrophysiologic tool (e.g., a guide wire, a catheter, a lead, stylet, etc.).

Also, for example, the dimension of the vascular branch may be defined at multiple locations along the length based on the known thickness of the tool, or the vibratory motion of the tool within the vascular branch, or the spatial resolution of visual images and the number of pixels across the visual images. Visual images may include fluoroscopic images, X-ray images, computed tomography (CT) scan or computed axial tomography (CAT) scan images, magnetic resonance imaging (MRI) images, ultrasound images, etc. In one example, a geometric data set is generated prospectively based on the known tool sizes and the visual images that are taken.

In one example, the visual images are enhanced with the use of a contrasting agent. In another example, the electrical and hemodynamic properties of pacing the heart at various locations (independently, simultaneously, or sequentially) within the vascular branch may also be characterized using an electrode on an electrophysiologic tool that can measure capture thresholds, cardiac performance, and determine and quantify diaphragmatic stimulation along the length of the vascular branch.

In one aspect, the vascular system (e.g., the cardiovascular system) may be characterized using one or more of the following: determining the length, angle and/or curvature characteristics of the vascular branches; determining the dimension (e.g., diameter) characteristics of the vascular branches; and/or determining the performance characteristics of the vascular branches (e.g., pacing capture thresholds, diaphragmatic stimulation characteristics, and other cardiac performances, etc.). With the information gained from characterizing the vascular system in terms of its dimensions (branch lengths and diameter), its curvatures, angles and contours, and its physiological characteristics before implantation of a permanent lead, medical personnel are better able to determine the optimum lead position, type, size and model to be used in a particular anatomy and good pacing sites within the branch.

In one example, a sensor's positional and orientation data are recorded as a tool with the sensor embedded on it is advanced along the length of a vascular branch. The position data and/or orientation data are used to measure the length of the vascular branch. Additionally, the sensor's trajectory path may include advancing from one vascular branch to other adjoining vascular branches so as to create a tree structure map of the vasculature system. In addition to branch lengths, bifurcation locations, branch angles and curvatures are defined from the sensor's position data and/or orientation data. In one example, one or more of the branch length, bifurcation location, branch angle and curvature characteristics is calculated by integration in 3-dimensions, either through piecewise integration or through continuous integration.

Figure 8:
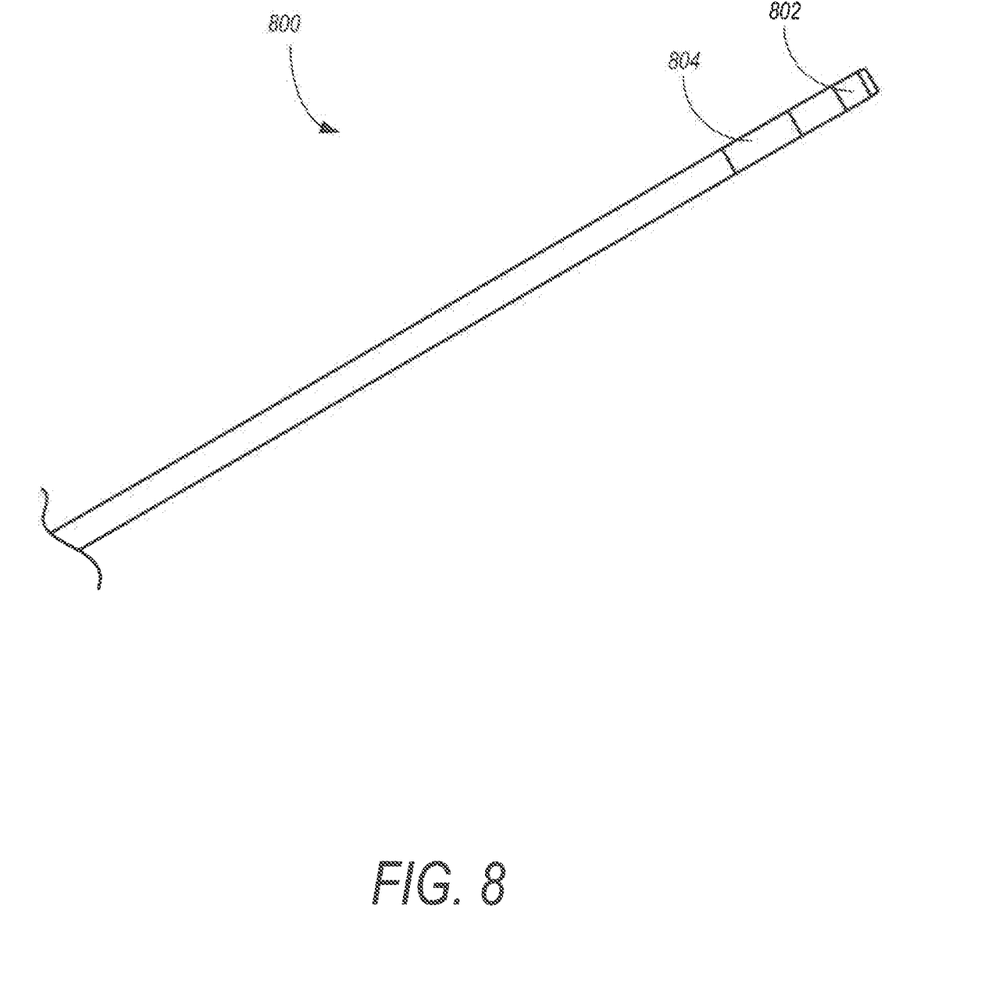
FIG. 8 illustrates an example lead implantable at a region of interest (ROI).

In one example, a medical personnel chooses among a few leads (e.g., bipolar or quadripolar leads) with different numbers of electrodes, handling characteristics, diameters, lengths and electrode spacing for permanent implantation in the vascular system of a patient. An example lead 800 having two electrodes 802, 804 is illustrated in FIG. 8. The medical personnel may determine which of the leads to choose using the sensors position data and/or orientation data. For example, as the tool with the embedded sensor leaves a vascular branch to enter another vascular branch, a mark is made to indicate location of the juncture. This mark may be indicated on a corresponding geometric data set of the patient's vascular system. In one example, the geometric data set is a map. When the tool with the embedded sensor first reaches a location that cannot be passed, for example, either because the vascular branch is too small or because the angle, curvature and/or contour of the vascular branch makes further passage impossible, a mark indicating such is made on that location. With the information derived from the sensors position data and/or orientation data and the marks made, the medical personnel can choose the lead with the most appropriate dimension and flexibility to meet the angle, curvature and/or contour challenges. And, the medical personnel can choose which one of the mapped vascular branches would be best suited for the implantation.

Figure 1:
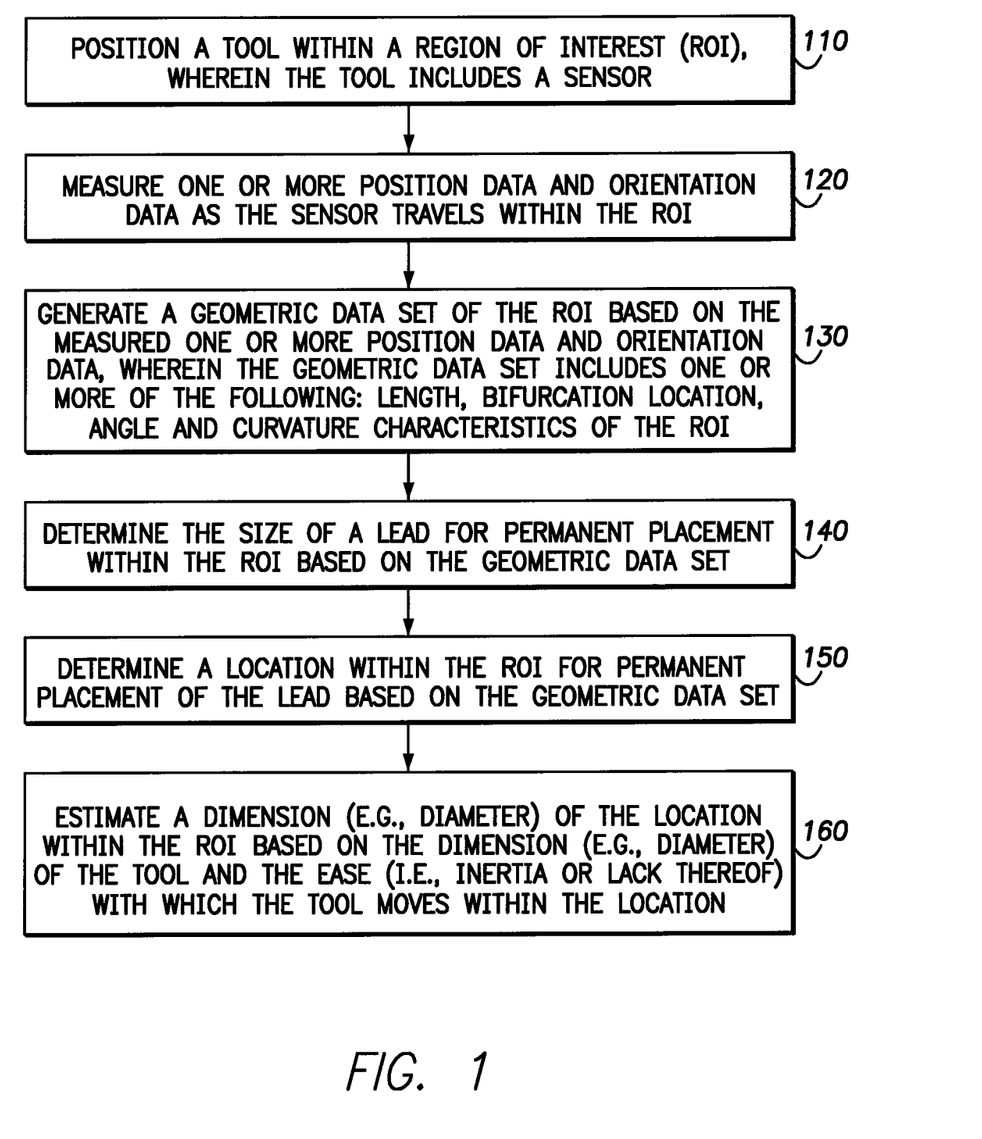
FIG. 1 illustrates a first example of a flow diagram for characterizing a region of interest (ROI).
Figure 7:
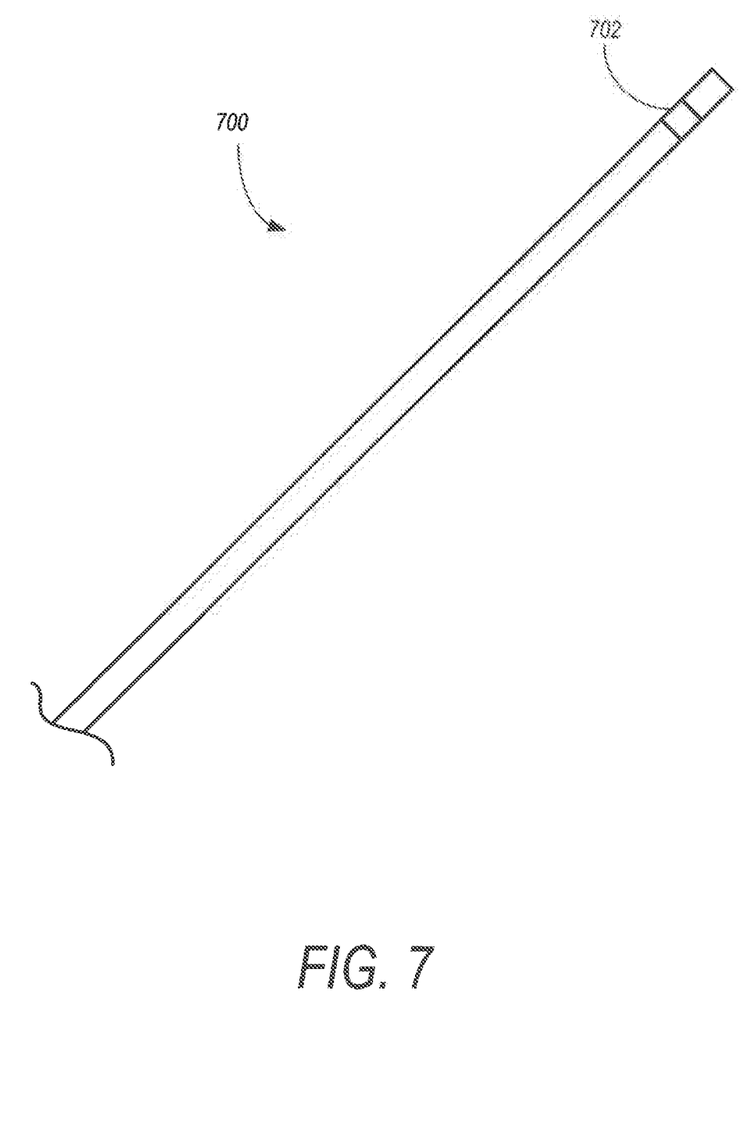
FIG. 7 illustrates an example tool for collecting vibratory motion data for characterizing a region of interest (ROI).

FIG. 1 illustrates a first example of a flow diagram for characterizing a region of interest (ROI). In block 110, position a tool within a region of interest (ROI), wherein the tool includes a sensor. In block 120, measure one or more position data and orientation data as the sensor travels within the ROI. In one example, the tool is one of the following: a catheter (e.g., are endocardial catheter, an epicardial catheter), a guide wire, a lead or a stylet. In one example, measurements of the position data and/or the orientation data are taken at intervals of spatial increments, angular increments or temporal increments. An example tool 700 including a sensor 702 is illustrated in FIG. 7.

In block 130, generate a geometric data set of the ROI based on the measured one or more position data and orientation data, wherein the geometric data set includes one or more of the following: length, bifurcation location, angle and curvature characteristics of the ROI. In one example, generating the geometric data set of the ROI comprises mapping one or more position data and orientation data onto an image of the ROI. In one example, one or more of the length, bifurcation location, angle and curvature characteristics is calculated by integration in 3-dimensions, either through piecewise integration or through continuous integration. In one example, the geometric data set is color-coded to indicate differences of one or more of the following: length, bifurcation location, angle and curvature characteristics of the ROI. In one example, the geometric data set corresponds to a map of the ROI.

In one example, a mark is made to indicate each location where the tool leaves one branch of the ROI and enters another branch of the ROI. The marks serve as markers at the junctions between two branches. The marks may be included in a geometric data set of the ROI. Examples of ROI may include cardiac veins, cardiac arteries, cerebral veins, cerebral arteries, peripheral veins, peripheral arteries, hepatic veins, hepatic arteries, renal arteries, renal veins, etc. Additionally, one skilled in the art would understand that the ROI need not be confined to blood vessels and may include any bodily cavity where a tool with an embedded sensor may travel through. This understanding of the ROI is equally applicable to all the examples of the present disclosure.

In one example, a mark is made to indicate a location where the tool leaving a first branch of the ROI is unable to enter a second branch of the ROI due to the size of the tool or an angular relationship between the first branch and the second branch. And, the size, shape or tool type of the tool may be recorded to correspond with the mark. In one example, the mark is indicated on a geometric data set of the ROI.

In block 140, determine the size of a lead for permanent placement within the ROI based on the geometric data set. In block 150, determine a location within the ROI for permanent placement of the lead based on the geometric data set. In block 160, estimate a dimension (e.g., diameter) of the location within the ROI based on the dimension (e.g., diameter) of the tool and the ease (i.e., inertia or lack thereof) with which the tool moves within the location. One skilled in the art would understand that, in one example, one or more of the steps in blocks 140, 150 and 160 may be optionally included with the steps in blocks 110-130, but may not be required.

In one aspect, the dimensions (e.g., diameter and length), take-off angle or tortuosity characteristic of a region of interest (ROI) may be calculated based on the known dimension(s) of the tool which may be used as a reference against the ROI dimensions. For instance, if the outer diameter (OD) of the tool is 8 Fr, then using a visual image, the diameter dimensions of the ROI as a proportion of the known OD of the tool may be estimated. And the length of the tool may be used to estimate a length dimension within the ROI. Additionally, the OD and length dimensions of the tool may be used to estimate the take-off angle or tortuosity characteristic of a region of interest (ROI). A geometric data set of the ROI may be generated, indicating the estimated dimensions (diameter and length), take-off angle and/or tortuosity characteristic of the ROI at various locations. The geometric data set may be used to develop a plan of where to place a permanent lead in the ROI in advance of the implantation procedure, and reduce or minimize trial-and-error implantations with different size and types of leads and delivery tools at different locations.

Figure 2:
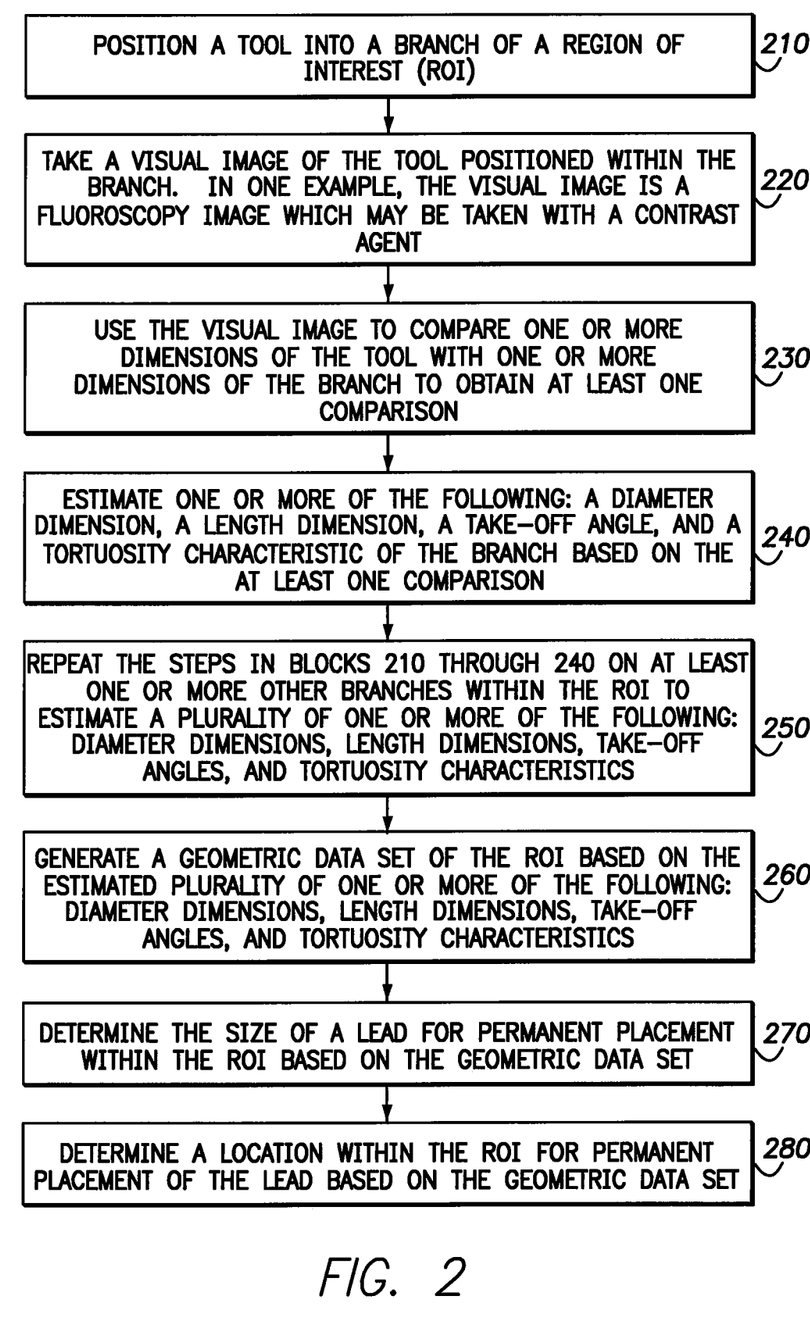
FIG. 2 illustrates a second example of a flow diagram for characterizing a region of interest (ROI).

FIG. 2 illustrates a second example of a flow diagram for characterizing a region of interest (ROI). In block 210, position a tool into a branch of a ROI. In one example, the tool is one of the following: a catheter (e.g., an endocardial catheter, an epicardial catheter), a guide wire, a lead or a stylet. Examples of ROI may include cardiac veins, cardiac arteries, cerebral veins, cerebral arteries, peripheral veins, peripheral arteries, hepatic veins, hepatic arteries, renal veins, renal arteries, etc. Additionally, one skilled in the art would understand that the ROI need not be confined to blood vessels and may include any bodily cavity through which a tool with an embedded sensor may travel.

In block 220, take a visual image of the tool positioned within the branch. In one example, the visual image is a fluoroscopy image which may be taken with a contrast agent. In another example, the visual image may be one of the following: an X-ray image, a computed tomography (CT) scan or computed axial tomography (CAT) scan image, a magnetic resonance imaging (MRI) image, an ultrasound image, etc. In block 230, use the visual image to compare one or more dimensions of the tool with one or more dimensions of the branch to obtain at least one comparison. In block 240, estimate one or more of the following: a diameter dimension, a length dimension, a take-off angle, and a tortuosity characteristic of the branch based on the at least one comparison. In the example where more than one visual images are taken at a location, the more than one visual images are taken at the same cardiac cycle and/or at the same respiratory cycle. In one example, the visual images as taken are gated to cardiac and/or respiratory motions or other periodic bodily motions.

In block 250, repeat the steps in blocks 210 through 240 on at least one or more other branches within the ROI to estimate a plurality of one or more of the following: diameter dimensions, length dimensions, take-off angles, and tortuosity characteristics. In block 260, generate a geometric data set of the ROI based on the estimated plurality of one or more of the following: diameter dimensions, length dimensions, take-off angles, and tortuosity characteristics. In one example, generating the geometric data set of the ROI comprises mapping one or more of the following: diameter dimensions, length dimensions, take-off angles, and tortuosity characteristics onto an image of the ROI. In one example, the geometric data set is color-coded on a map of the ROI to indicate differences among one or more of diameter dimensions, length dimensions, take-off angles, and tortuosity characteristics for better visualization.

In block 270, determine the size of a lead for permanent placement within the ROI based on the geometric data set. In block 280, determine a location within the ROI for permanent placement of the lead based on the geometric data set. One skilled in the art would understand that, in one example, one or more of the steps in blocks 250, 260, 270 and 280 may be optionally included with the steps in blocks 210 through 240, but may not be required.

In one aspect, the characteristics of a blood vessel may be estimated using the vibratory motion (e.g., bouncing motion) of a tool inserted into the blood vessel. The vibratory motion of the tool may occur at high frequency due to the mechanical motion of the heart and the stiffness of the tool. As the heart beats, the indwelling sensor that is embedded on the tool moves with the heartbeats, but can also include some "whip" or "bounce" within the blood vessel (e.g., a cardiac vein, the coronary sinus (CS), etc.). The wideband motion of the sensor represents the superposition of the real cardiac motions and the "whip" or "bounce" within the blood vessel. The vibratory motion data may be collected by collecting position data and/or orientation data at a high sample rate, extracting the cardiac and respiratory motion, and integrating time spent by the sensor at different positions. Characteristics of the blood vessel may be estimated based on the amount of high frequency vibratory motion of the sensor and used as indication of the blood vessel's suitability for a lead implantation and used to help choose the size and/or type of lead for the implantation.

In one example, more than one blood vessel is characterized, and a geometric data set is generated to indicate the characteristics of the blood vessels based on the vibratory motion of the sensor at various locations. In one example, the geometric data set is color-coded on a map of the ROI to indicate differences in the amplitude of the vibratory motion or in the frequencies of the vibratory motion.

Figure 3:
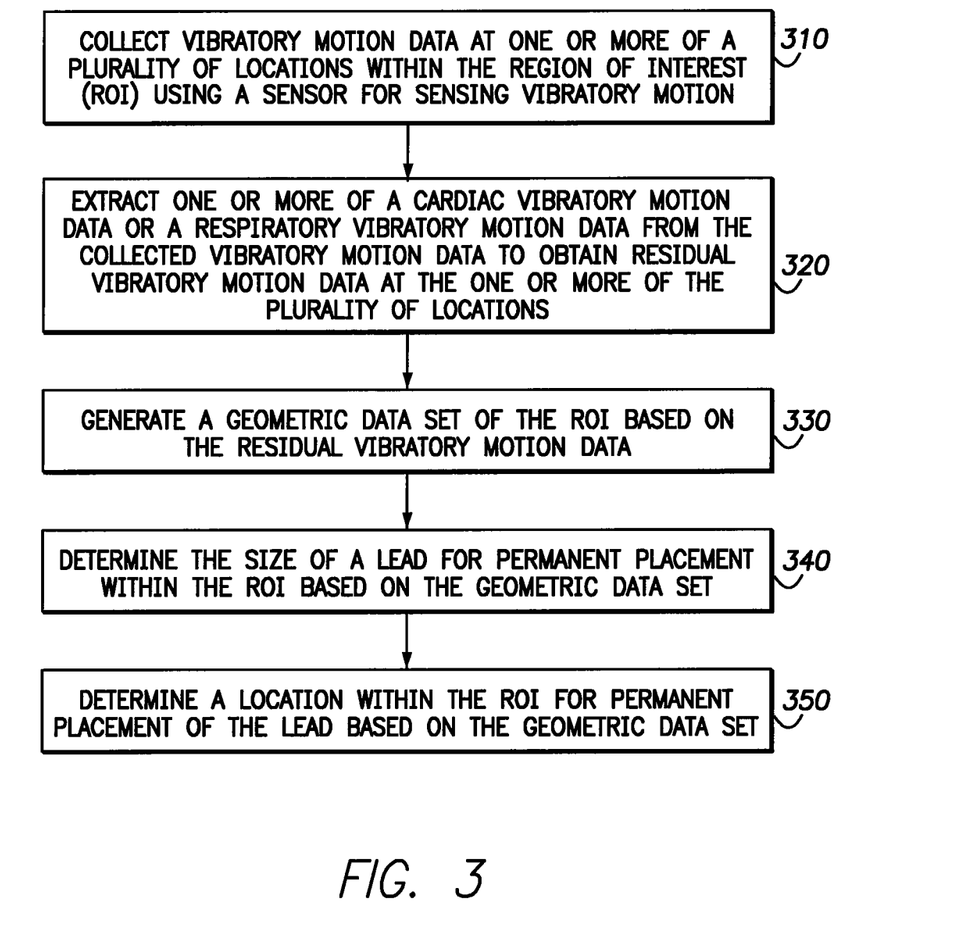
FIG. 3 illustrates a third example of a flow diagram for characterizing a region of interest (ROI).

FIG. 3 illustrates a third example of a flow diagram for characterizing a region of interest (ROI). In block 310, collect vibratory motion data at one or more of a plurality of locations within the region of interest (ROI) using a sensor for sensing vibratory motion. The vibratory motion data may be collected at a sample rate, for example, at the Nyquist rate or greater than the Nyquist rate. In one example, the sensor is embedded on a tool. The tool may be one of the following: an endocardial catheter, an epicardial catheter, a guide wire, a lead and a stylet. The tool may be floppy in the radial direction, allowing for collecting vibratory motions. And, in one example, as the tool with the embedded sensor is advanced through the plurality of locations within the ROI, a continuous picture of the cross sectional area dimensions of the ROI is revealed.

In block 320, extract one or more of a cardiac vibratory motion data or a respiratory vibratory motion data from the collected vibratory motion data to obtain residual vibratory motion data at the one or more of the plurality of locations. In block 330, generate a geometric data set of the ROI based on the residual vibratory motion data. In one example, generating the geometric data set of the ROI comprises mapping the residual vibratory motion data onto an image of the ROI. Typically, greater residual vibratory motion is an indication of larger diameter dimension or larger cross-sectional area of the ROI. The geometric data set may be color-coded on a map of the ROI to indicate one or more of amplitude of residual vibratory motion, diameter dimension and/or cross sectional area.

In block 340, determine the size of a lead for permanent placement within the ROI based on the geometric data set. In block 350, determine a location within the ROI for permanent placement of the lead based on the geometric data set. One skilled in the art would understand that, in one example, one or more of the steps in blocks 340 and 350 may be optionally included with the steps in blocks 310 through 330, but may not be required.

In one example, the cardiac vibratory motion data and/or the respiratory vibratory motion data (as mentioned in block 320) is measured independently by a second sensor. In another example, a force is applied to stiffen the tool and measure the vibration experienced by the stiffened tool. Then, use the measured vibration as the cardiac vibratory motion data and/or the respiratory vibratory motion data to be extracted from the collected vibratory motion data to obtain the residual vibratory motion data.

In yet another example, the cardiac vibratory motion data and/or the respiratory vibratory motion data is extracted by filtering (e.g., using a fast Fourier transform (FFT) algorithm) the collected vibratory motion data to obtain the residual vibratory motion data. Typically, the cardiac vibratory motion data and/or the respiratory vibratory motion data is comprised of low frequency harmonics of fundamental frequencies (e.g., approximately 1 Hz for cardiac vibratory motion and less than 1 Hz for respiratory vibratory motion) and the residual vibratory motion data is comprised of higher frequency components (e.g., 3-20 Hz).

Figure 4:
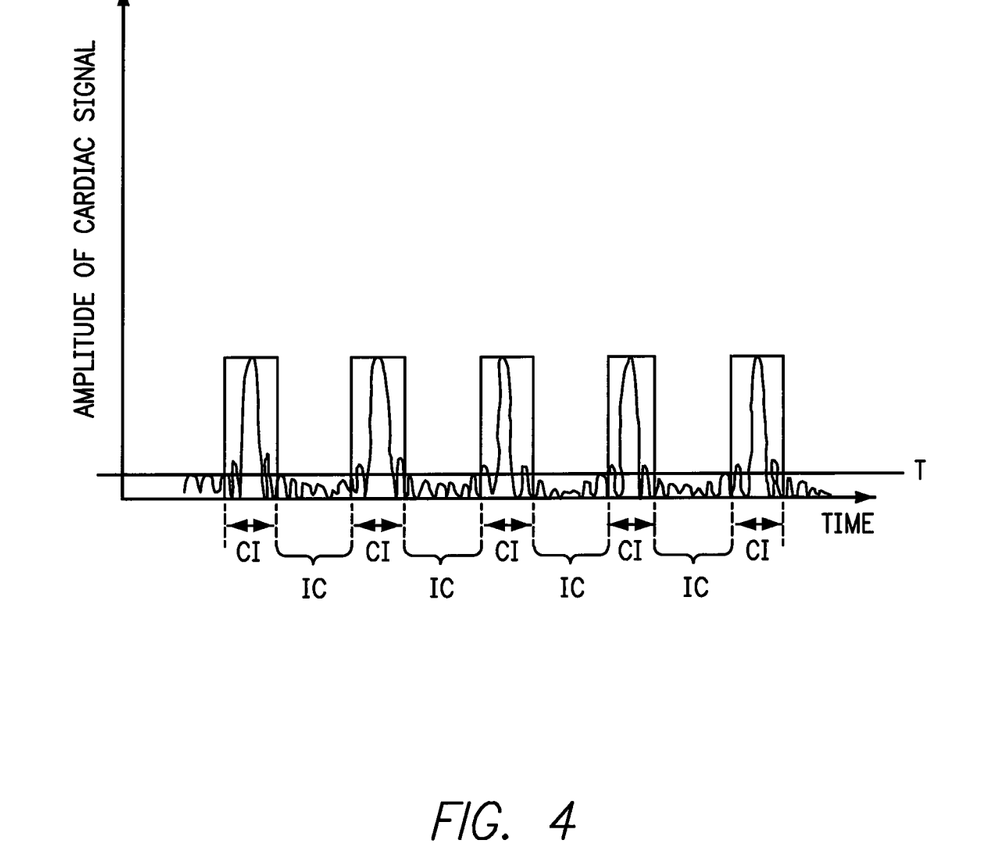
FIG. 4 illustrates an example graph depicting amplitude of cardiac signals versus time.

In yet another example, the extraction of cardiac vibratory motion data and/or the respiratory vibratory motion data from collected vibratory motion data to obtain residual vibratory motion data includes gating the collected vibratory motion data by synchronizing to cardiac signals and collecting vibratory motion data only during inter-cardiac durations when the collected vibratory motion data is free or minimized from cardiac vibratory motion data and/or the respiratory vibratory motion data. Thus, the collected vibratory motion data is approximately the residual vibratory motion data if collected during the inter-cardiac durations. FIG. 4 illustrates an example graph depicting amplitude of cardiac signals versus time. As shown in FIG. 4, IC represents the inter-cardiac durations while CI represents the cardiac interval durations. As defined in FIG. 4, the inter-cardiac (IC) durations represent the time durations during which the amplitude of the cardiac signal is below a threshold T, and the cardiac interval (CI) durations represent the time durations during which the amplitude of the cardiac signal is at or over the threshold T. One skilled in the art would understand that the value of the threshold T may be chosen based on many factors, including but not limited to, accuracy considerations, such as, for gating the cardiac signal and the accuracy requirement of the residual vibratory motion data based on its intended application, or on a background noise level. One skilled in the art would understand that the cardiac signal can be an original signal measured by the instruments or a signal derived from other signals (e.g. a derivative of another cardiac signal, or a combination of various cardiac signals).

In one aspect, a temporary pacing lead may be used to identify an efficacious location for permanent pacing. In particular, pacing may be attempted at each of multiple sites along a branch within a region of interest (ROI) to evaluate capture threshold, presence of diaphragmatic stimulation and/or cardiac performance. At each location, for example, pacing the ventricle individually or in combination with another lead (such as a typical right ventricular (RV) lead), various outcomes of left ventricular (LV) or bi-ventricular (BiV) pacing may be determined. The results of the temporary pacing may be assessed and utilized to provide a more descriptive geometric data set on the venogram depicting suitable implant sites for the permanent pacing electrode. And, the geometric data set may be color-coded to mark one or more optimal locations for permanent lead implantation or to exclude undesirable zones with diaphragmatic stimulation, high capture threshold requirements, or poor cardiac performance.

Figure 5:
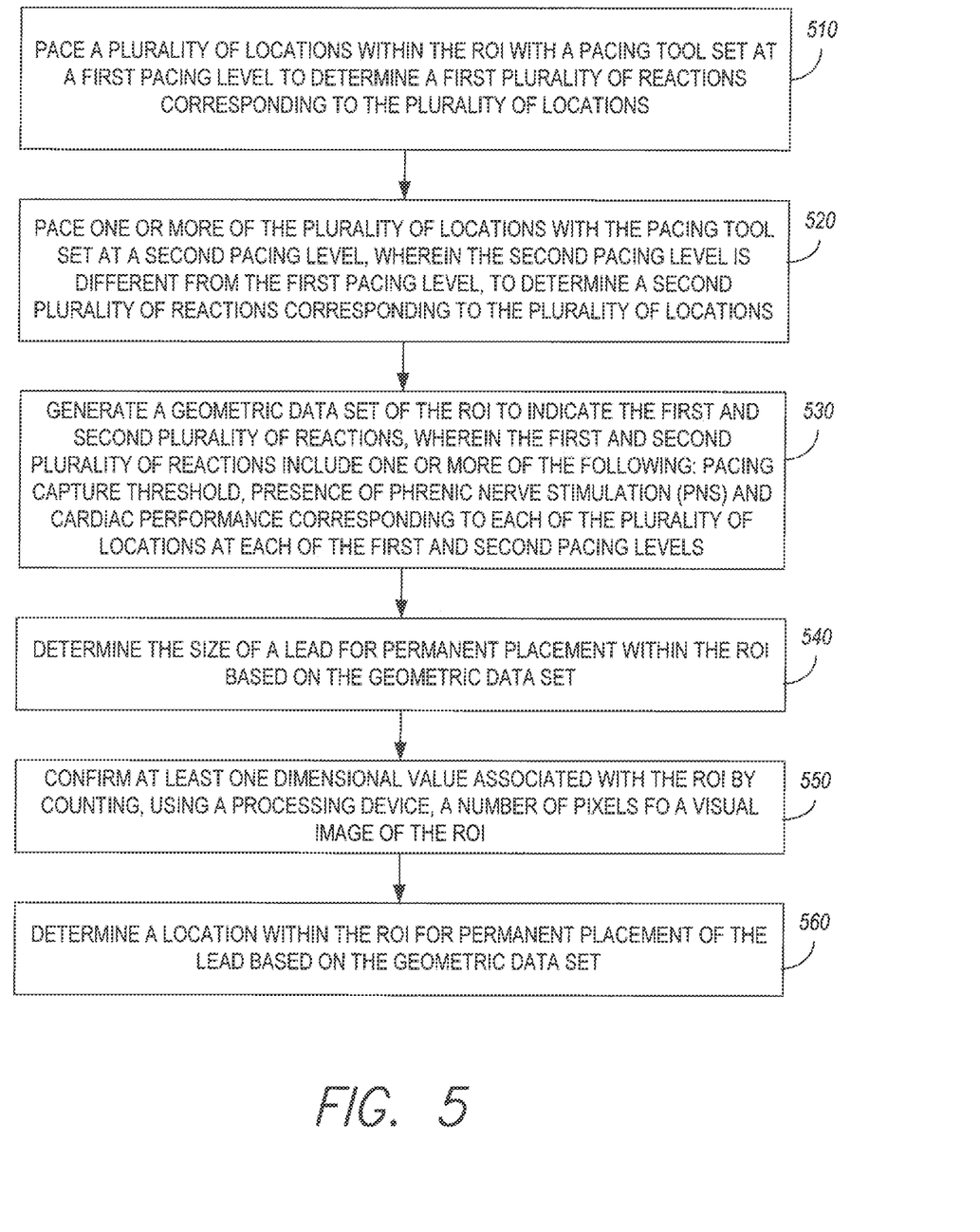
FIG. 5 illustrates a fourth example of a flow diagram for characterizing a region of interest (ROI).

FIG. 5 illustrates a fourth example of a flow diagram for characterizing a region of interest (ROI). In block 510, pace a plurality of locations within the ROI with a pacing tool set at a first pacing level to determine a first plurality of reactions corresponding to the plurality of locations. In one example, the pacing tool is a temporary pacing lead. In one example, the pacing is performed with more than one temporary pacing lead. And, the temporary pacing lead or multiple temporary pacing leads used may include one or more of a left ventricular (LV) lead, a right ventricular (RV) lead. In one example, the first plurality of reactions includes one or more of the following: pacing capture threshold, presence of diaphragmatic stimulation and cardiac performance.

In block 520, pace one or more of the plurality of locations with the pacing tool set at a second pacing level, wherein the second pacing level is different from the first pacing level, to determine a second plurality of reactions corresponding to the plurality of locations. In another example, the second pacing level is greater than the first pacing level. In one example, the second plurality of reactions includes one or more of the following: pacing capture threshold, presence of diaphragmatic stimulation and cardiac performance. In one example, the first and second pacing levels may range from a few tenths of a volt to 5 to 10 volts. Different values of the pacing level may be tried to determine a pacing level that will stimulate the heart.

In block 530, generate a geometric data set of the ROI to indicate the first and second plurality of reactions, wherein the first and second plurality of reactions include one or more of the following: pacing capture threshold, presence of diaphragmatic stimulation and cardiac performance corresponding to each of the plurality of locations at each of the first and second pacing levels. Examples of cardiac performance may include one or more measurements of stroke volume, cardiac output, cardiac contractility and/or cardiac dyssynchrony. In one example, the geometric data set shows a visual representation of cardiac performance based on pacing site. In one example, generating the geometric data set of the ROI comprises mapping the first and second plurality of reactions onto an image of the ROI.

The phrenic nerve is a nerve that passes along the heart to reach the diaphragm. The phrenic nerve is associated with breathing, and it passes motor information to the diaphragm and receives sensory information from it. Thus, it is desirable to know the location of the phrenic nerve and the stimulus magnitude that would cause diaphragmatic stimulation. In one example, the geometric data set contains a visual representation of diaphragmatic stimulus magnitude.

Stroke volume is the amount of blood ejected by the left ventricle each heartbeat. In one example, stroke volume is measured through the use of one or more sensors within the thorax. As pacing may be accomplished from each of multiple locations over the left and right ventricles, the resulting stroke volume measured or estimated from pacing from each of these locations may be performed and displayed on a geometric data set of the ROI.

Cardiac contractility is the ability of the left ventricle to generate the force of mechanical contraction to eject blood from the left ventricle. Cardiac contractility may be decreased because of ventricular dys-synchrony. Ventricular dys-synchrony is a cardiac condition wherein the activation of different parts of the ventricles is not properly synchronized, and the pressure generated by the left ventricle (LV) to eject blood is compromised.

In block 540, determine the size of a lead for permanent placement within the ROI based on the geometric data set. In block 560, determine a location within the ROI for permanent placement of the lead based on the geometric data set. In one example, the geometric data set corresponds to a map of the ROI. The geometric data set provides a visual representation of potential pacing sites. In one example, the geometric data set may provide a spatial representation of pacing capture threshold, the minimum level of energy or voltage required to cause a cardiac evoked response.

In one example, the geometric data set is color-coded to indicate one or more graded locations for lead implantation. For example, the "grade" of the location may indicate a spectrum of desirable locations to undesirable locations within the ROI for lead implantation. In another example, the geometric data set is color-coded to indicate one or more of the following reactions: pacing capture threshold, presence of diaphragmatic stimulation and cardiac performance obtained by pacing at each of the plurality of locations. The color code may also indicate different pacing levels.

In one aspect and as included in block 550 of the method of FIG. 5, dimensions of the region of interest (ROI) may be calculated or confirmed using one or more visual images (e.g., fluoroscopic images, X-ray images, computed tomography (CT) scan or computed axial tomography (CAT) scan images, magnetic resonance imaging (MRI) images, ultrasound images, etc.). For example, the visual images have a known spatial resolution such that a given pixel in the visual images represents a given measurement in physical space. As such, the cross-sectional area (e.g., diameter or length) of a particular branch of the ROI that is filled with a contrast agent may be calculated using pixel by pixel image processing techniques and by counting the number of pixels depicted within the branch boundaries. For example, a geometric data set of the entire vascular system may then be created after dimensional measurements (e.g., diameter or length measurements) are completed for a plurality of branches to indicate the dimensions of the ROI. In one example, the geometric data set is color-coded based on the dimensional measurements, indicating for example, maximum sizes of candidate implanting leads, and/or indicating to the implanting medical personnel to what depth a lead can reach inside a particular branch (e.g., blood vessel). In one example, the geometric data set may show possible lead locations based on blood vessel dimensions (e.g., diameters). For example, the geometric data set may be presented on a map, and darker colors on the map would indicate smaller blood vessel dimensions (e.g., diameters).

In the present disclosure, the sensor mentioned in each of the examples may be an electromagnetic sensor, an ultrasonic sensor or any other type of sensor that provides the data disclosed in each of the examples. Additionally, one skilled in the art would understand that the different examples disclosed herein may be used in combination with any of the other examples without departing from the scope and spirit of the present disclosure.

Figure 6:
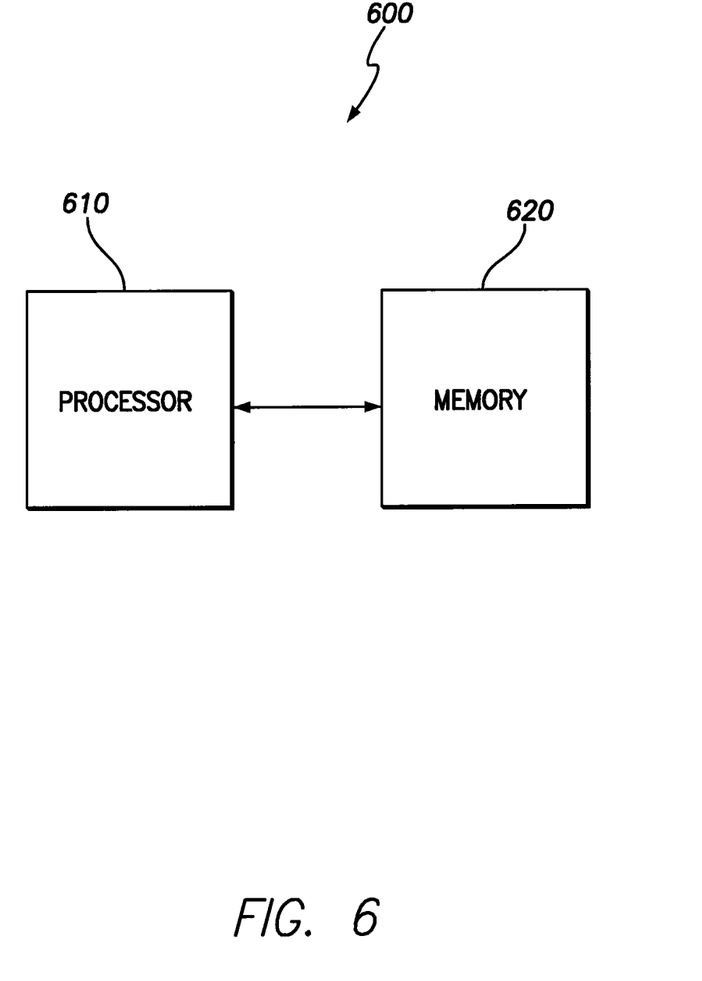
FIG. 6 illustrates an example of a device comprising a processor in communication with a memory for executing the processes of characterizing a region of interest (ROI).

FIG. 6 illustrates an example of a device 600 comprising a processor 610 in communication with a memory 620 for executing the processes of characterizing a region of interest (ROI). In one example, the device 600 is used to implement the algorithms illustrated in FIGS. 1-3 and 5. In one aspect, the memory 620 is located within the processor 610. In another aspect, the memory 620 is external to the processor 610. In one aspect, the processor includes circuitry for implementing or performing the various flow diagrams, logical blocks and/or modules described herein.

While for purposes of simplicity of explanation, the methodologies are shown and described as a series of acts, it is to be understood and appreciated that the methodologies are not limited by the order of acts, as some acts may, in accordance with one or more aspects, occur in different orders and/or concurrently with other acts from that shown and described herein. For example, those skilled in the art will understand and appreciate that a methodology could alternatively be represented as a series of interrelated states or events. Moreover, not all illustrated acts may be required to implement a methodology in accordance with one or more aspects.

The previous description of the disclosed aspects is provided to enable any person skilled in the art to make or use the present disclosure. Various modifications to these aspects will be readily apparent to those skilled in the art, and the generic principles defined herein may be applied to other aspects without departing from the spirit or scope of the disclosure.

What is claimed is:

1. A method for characterizing a region of interest (ROI) comprising:

advancing a tool through one or more locations within the ROI: and at each of the one or more locations within the ROI:

collecting vibratory motion data using an electromagnetic sensor for sensing vibratory motion, wherein the electromagnetic sensor is embedded on the tool;

applying a processor to extract one or more of cardiac vibratory motion data or respiratory vibratory motion data from the collected vibratory motion data to obtain residual vibratory motion data at the one or more locations;

applying a processor to generate geometric data of a geometric data set of the ROI based on the residual vibratory motion data;

determining a cross-sectional area dimension at the one or more locations based on the geometric data set; and determining a size of a lead for permanent placement within the ROI based on the geometric data set.

2. The method of claim 1, further comprising determining a location within the ROI for permanent placement of a lead based on the geometric data set.

3. The method of claim 1, wherein the vibratory motion data is collected at or greater than a Nyquist rate of the electromagnetic sensor.

4. The method of claim 1, wherein the ROI comprises one or more of the following: a cardiac vein, a cardiac artery, a cerebral vein, a cerebral artery, a peripheral vein, a peripheral artery, a hepatic vein, a hepatic artery, a renal vein and a renal artery.

5. The method of claim 4, further comprising confirming at least one dimensional value associated with the ROI by counting, using a processing device, a number of pixels of a visual image of the ROI, wherein the visual image is one of a fluoroscopic image, an X-ray image, a computed tomography scan, a computed axial tomography scan, a magnetic resonance imaging image, or an ultrasound image.

6. The method of claim 1, further comprising determining a location within the ROI for permanent placement of a lead based on the geometric data set.

7. The method of claim 1, wherein the applying the processor includes extracting the cardiac vibratory motion data from the collected vibratory motion data to obtain the residual vibratory motion data at the one or more locations.

8. The method of claim 1, wherein the residual vibratory motion data does not include the cardiac vibratory motion data.

9. The method of claim 1, wherein the residual vibratory motion data differs from the cardiac vibratory motion data.

* * * * *